US00PP21008P2

(12) United States Plant Patent
Schoemaker

(10) Patent No.: US PP21,008 P2
(45) Date of Patent: May 25, 2010

(54) ***HYDRANGEA* PLANT NAMED 'BOMBSHELL'**

(50) Latin Name: *Hydrangea paniculata*
Varietal Denomination: Bombshell

(76) Inventor: Alex Frederik Schoemaker, Rijneveld 37, NL-2771 XX Boskoop (NL)

( * ) Notice: Subject to any disclaimer, the term of this patent is extended or adjusted under 35 U.S.C. 154(b) by 0 days.

(21) Appl. No.: 12/383,527

(22) Filed: Mar. 25, 2009

(51) Int. Cl.
*A01H 5/00* (2006.01)

(52) U.S. Cl. ..... Plt./250
(58) Field of Classification Search ..... Plt./250
See application file for complete search history.

*Primary Examiner*—Kent L Bell
(74) *Attorney, Agent, or Firm*—Penny J. Aguirre

(57) ABSTRACT

A new cultivar of *Hydrangea paniculata* named 'Bombshell' that is characterized by its panicles that are nearly rounded in shape, its abundance of sterile flowers with sepals that are elliptic in shape and emerge white with a pink eye and changing to rosy pink as they mature, its free blooming habit from mid summer to fall, and its compact growth habit.

2 Drawing Sheets

Genus/species: *Hydrangea paniculata.*
Varietal denomination: 'Bombshell'.

BACKGROUND OF THE INVENTION

The present invention relates to a new and distinct cultivar of *Hydrangea paniculata* and will be referred to hereafter by its cultivar name, 'Bombshell'. 'Bombshell' represents a new panicle *hydrangea,* a deciduous shrub grown for landscape use.

'Bombshell' was discovered by the Inventor in his nursery in Boskoop, The Netherlands in May of 2003. 'Bombshell' arose as a naturally occurring branch mutation on *Hydrangea paniculata* 'Grandiflora' (not patented) that was growing in a container.

Asexual reproduction of the new cultivar was first accomplished by softwood stem cuttings by the Inventor in Boskoop, The Netherlands in July of 2003. The characteristics of this cultivar have been determined to be stable and are reproduced true to type in five successive generations.

SUMMARY OF THE INVENTION

The following traits have been repeatedly observed and represent the characteristics of the new cultivar. These attributes in combination distinguish 'Bombshell' as a unique cultivar of *Hydrangea paniculata.*

1. 'Bombshell' exhibits inflorescences with an abundance of sterile flowers with sepals that are elliptic in shape and emerge white with a pink eye and changing to rosy pink as they mature.
2. 'Bombshell' exhibits panicles that are nearly round in shape.
3. 'Bombshell' exhibits a free flowering habit and blooms from mid summer through fall in The Netherlands.
4. 'Bombshell' exhibits a very compact growth habit.

The new cultivar of *Hydrangea* differs from its parent plant, 'Grandiflora', in having more rounded inflorescences, in having more abundant blooms and in having a more compact growth habit. 'Bombshell' can be compared to the cultivar 'Barbara' (U.S. Plant Pat. No. 13,606), which is similar in inflorescence color, however 'Barbara' differs in having a greater number of fertile flowers, larger and fewer sterile flowers with oblanceolate shaped sepals, panicles that are less rounded in shape, and a more arching plant habit. 'Bombshell' can also be compared to 'White Moth' (not patented), which has a similar inflorescence color and blooming habit. 'White Moth' differs from 'Bombshell' however, in having irregular-shaped inflorescences that remain white in color throughout floral development and have a greater number of fertile flowers and in developing into a larger sized and less compact plant.

BRIEF DESCRIPTION OF THE DRAWINGS

The accompanying photographs were taken of a two year-old plant of 'Bombshell' as grown outdoors in a 7.5-liter container in Boskoop, The Netherlands.

The photograph in FIG. 1 illustrates the plant habit and flowers of 'Bombshell' in bloom in November.

Figure 1:
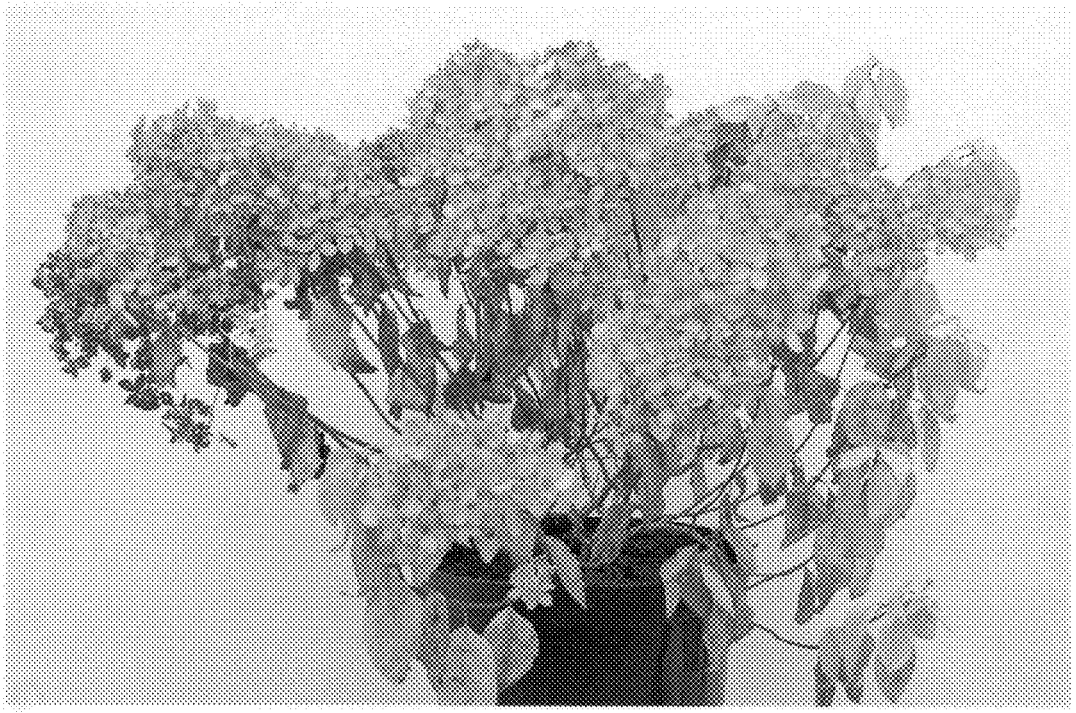
Figure 2:
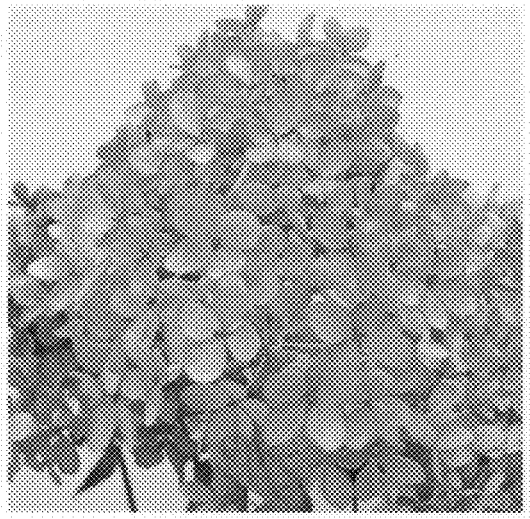

The photograph in FIG. 2 provides a close-up view of a fully mature inflorescence of 'Bombshell' in November.

Figure 3:
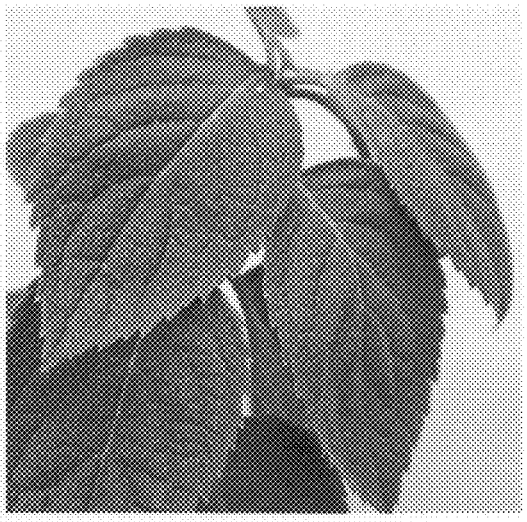

The photograph in FIG. 3 provides a close-up view of the leaves of 'Bombshell' as growing in late summer.

Figure 4:
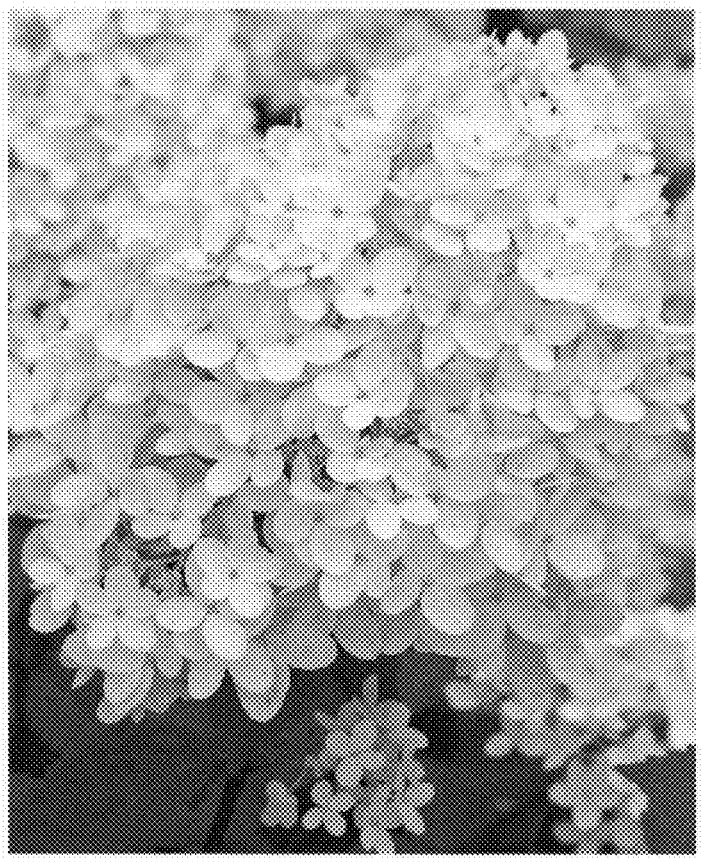

The photograph in FIG. 4 provides a close-up view of an inflorescence of 'Bombshell' in late summer.

The colors in the photographs may differ slightly from the color values cited in the detailed botanical description, which accurately describe the colors of the new *Hydrangea.*

BOTANICAL DESCRIPTION OF THE PLANT

The following is a detailed description of two year-old plants of the new cultivar as grown outdoors in a 7.5-liter container in Boskoop, The Netherlands. Phenotypic differences may be observed with variations in environmental, climatic, and cultural conditions. The color determination is in accordance with the 2007 R.H.S. Colour Chart of The Royal Horticultural Society, London, England, except where general color terms of ordinary dictionary significance are used.

General description:

*Blooming period.*—Blooms continuously from mid summer to fall in Boskoop, The Netherlands.

*Plant habit.*—Broadly upright, overall plant shape is globular.

*Height and spread.*—Reaches about 41.5 cm in height and 67.5 width at 2 years in age.

*Hardiness.*—U.S.D.A. Zones 4 to 9.

*Diseases.*—No susceptibility or disease resistance has been observed.

*Environmental tolerance.*—Panicles exhibit good tolerance to wind and rain.

*Root description.*—Fibrous and dense.

*Growth rate.*—Moderate.

Growth and propagation:

*Propagation.*—Softwood stem cuttings, division of mature plants is also possible.

*Root initiation.*—About 4 weeks in summer under greenhouse conditions with 20° C. days and 18° C. nights and 5 weeks in winter with 12° C. days and 8° C. nights.

*Finishing time.*—Average of 12 months from propagation to finishing in a 2-liter container.

Stem description:

*Stem shape.*—Round, solid.

*Stem strength.*—Strong.

*Stem aspect.*—Upright to 45°.

*Stem color.*—New growth; N199A to 199A, mature; to N199B to 199C.

*Stem size.*—Average of 23.1 cm in length, average of 3 mm in width.

*Stem surface.*—Pubescent, immature stems are sparsely covered with short adpressed hairs averaging 1 mm in length and N155A in color.

*Internode length.*—Average of 4.9 cm.

*Branching.*—Freely branched, a two year-old plant will produce an average of 44 lateral branches, pinching improves branching.

Foliage description:

*Leaf shape.*—Ovate.

*Leaf arrangement.*—Opposite.

*Leaf division.*—Simple.

*Leaf base.*—Broadly cuneate to rounded.

*Leaf apex.*—Acute.

*Leaf margins.*—Serrate.

*Leaf venation.*—Pinninerved, recessed on upper surface, color 144A to 144B on upper surface and 147D to 148D with an overlay of 187C towards base of vein on lower surface.

*Leaf size.*—Average of 6.2 cm in length and 3.7 cm in width.

*Leaf attachment.*—Petiolate.

*Leaf surface.*—Upper and lower surfaces; dull, slightly rugose, moderately pubescent, and covered with short adpressed hairs averaging 1 mm in length and 157D in color.

*Leaf color.*—Upper surface N137B, lower surface 138B.

*Petioles.*—Average of 1.1 cm in length and 1.5 mm in width, dull in texture, moderately pubescent with very short hairs about 0.8 mm in length and 157C to 157D in color, upper surface 183A to 183B in color, lower surface 187C in color.

Inflorescence description:

*Inflorescence type.*—Terminal panicles in a nearly rounded form comprised of rotate, star-shaped sterile flowers above mostly hidden fertile flowers.

*Lastingness of inflorescence.*—Persistent, but summer color is retained for about 4 weeks.

*Inflorescence number.*—One per lateral or sublateral stem if pinched.

*Inflorescence size.*—Average of 13.7 cm in height and 11.9 cm in diameter.

*Flower number.*—Numerous, average of about 200 sterile flowers and about 90 fertile flowers per inflorescence.

*Flower fragrance.*—None.

*Flower aspect.*—Upright to outward.

*Flower size.*—Sterile flowers; an average of 3 cm in diameter and 1.1 cm in depth.

*Flower buds* (*sterile flowers*).—An average of 4 mm in length and 3 mm in width, globose in shape, 155C in color, glabrous surface.

*Peduncles.*—Strong, extension of stem, average of 6 cm in length and 2 mm in width, N199B to 199C in color, surface is pubescent.

*Pedicels.*—Sterile flowers; moderate strength, an average of 1.7 mm in length and 1 mm in width, 157A in color and changing to 182D, surface is smooth and dull held between 50° and 110° angle, averaging 75°, fertile flowers; an average of 4 mm in length and 0.5 mm in length, moderate in strength, texture is smooth, dull.

*Fertile flowers.*—145D to 155A in color in general with sepals 144A in color, primarily hidden by sterile flowers, an average of 7 mm in diameter and 6 mm in depth, rotate in shape, lasting about 7 days on the plant, not persistent on the plant (self cleaning), non-fading.

*Sepals* (*sterile flowers*).—4, occasionally 5, un-fused, rotate in arrangement, smooth, dull and glabrous on both surfaces, primarily elliptic in shape, held nearly flat when fully open, entire margin, apex is rounded to shortly acute, average of 1.5 cm in length and 1.1 cm in width, color upper and lower surface when newly opened, upper and lower surface; 155A to 155C, color when mature, upper surface; 177D overlayed with 182D, color when mature, lower surface; 182B to 182C in color.

*Center* (*eye of sterile flowers*).—1.5 mm in diameter, 182C to 177D in color.

Reproductive organs (fertile flowers):

*Stamens.*—Average of 10, anther is about 1 mm in length and 145D in color, filament is an average of 4 mm in length and 155A in color, pollen was not observed.

*Pistils.*—Average of 3, average of 2.5 mm in length, 145D in color, style is an average of 2 mm in length, stigma is flattened on the of the style and 155A in color.

*Fruit and seed.*—None observed.

It is claimed:

1. A new and distinct cultivar of *Hydrangea* plant named 'Bombshell' substantially as herein illustrated and described.

* * * * *